United States Patent [19]

Loeffler et al.

[11] 4,405,614
[45] Sep. 20, 1983

[54] N-SULFONYLATED THIOLPHOSPHORIC ESTER AMIDES AND THEIR USE FOR CONTROLLING PESTS

[75] Inventors: Hans-Peter Loeffler; Walter Seufert, both of Ludwigshafen; Heinrich Adolphi, Limburgerhof, all of Fed. Rep. of Germany

[73] Assignee: BASF Aktiengesellschaft, Fed. Rep. of Germany

[21] Appl. No.: 356,722

[22] Filed: Mar. 10, 1982

[30] Foreign Application Priority Data

Mar. 27, 1981 [DE] Fed. Rep. of Germany ....... 3112064

[51] Int. Cl.³ .......................... C07F 9/24; A01N 57/28
[52] U.S. Cl. .................................... 424/215; 260/947
[58] Field of Search .......................... 260/947; 424/215

[56] References Cited

U.S. PATENT DOCUMENTS 4,134,979  1/1979  Kishino et al. ...................... 424/215
4,150,155  4/1979  Kishino et al. ...................... 424/216

FOREIGN PATENT DOCUMENTS 3112064 10/1982 Fed. Rep. of Germany .

Primary Examiner—Anton H. Sutto
Attorney, Agent, or Firm—Keil & Witherspoon

[57] ABSTRACT

N-sulfonylated thiolphosphoric ester amides of the formula

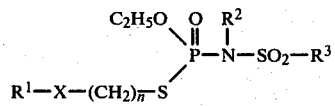

where $R^1$, $R^2$, $R^3$, X and n have the meanings given in the description, and their use for controlling insects, arachnida and nematodes.

9 Claims, No Drawings

N-SULFONYLATED THIOLPHOSPHORIC ESTER AMIDES AND THEIR USE FOR CONTROLLING PESTS

The present invention relates to N-sulfonylated thiolphosphoric ester amides, insecticides, acaricides and nematicides containing these active compounds, and methods for controlling insects, arachnida and nematodes.

N-Sulfonylated thiolphosphoric ester amides having insecticidal, acaricidal and nematicidal action have been disclosed inter alia in German Laid-Open Application DOS No. 2,642,054.

We have found that N-sulfonylated thiolphosphoric ester amides of the formula

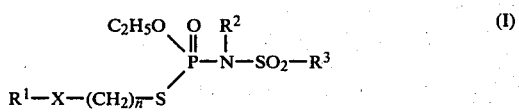

where $R^1$ is alkyl of 1 to 3 carbon atoms, $R^2$ is alkyl or alkenyl of up to 6 carbon atoms, $R^3$ is alkyl or haloalkyl of 1 to 6 carbon atoms or dialkylamino where alkyl is of 1 to 6 carbon atoms, X is oxygen or sulfur, and n is 1 or 2, possess extraordinarily powerful insecticidal, acaricidal and nematicidal activity and have a superior action to known N-sulfonylated thiolphosphoric ester amides.

In particular, they exhibit a good action against caterpillars, Rhodnius bugs and spider mites.

Suitable alkyl radicals $R^1$, $R^2$ and $R^3$ in formula I are straight-chain or branched and of up to 3 or 6 carbon atoms, for example methyl, ethyl, n-propyl or i-propyl for $R^1$, $R^2$ or $R^3$, and also n-butyl, i-butyl, n-pentyl or i-hexyl for $R^2$ or $R^3$. $R^3$ can also be haloalkyl of up to 6 carbon atoms, eg. chloromethyl, bromomethyl, 2-chloroethyl, 2-bromoethyl, 3-chloro-n-propyl, 4-chloro-n-butyl, 1-methyl-2-chloro-n-propyl or 1-chloromethyl-ethyl, in particular chloromethyl, or dialkylamino where alkyl is of 1 to 6 carbon atoms, eg. dimethylamino, diethylamino, diisopropylamino or methylethylamino.

The N-sulfonylated thiolphosphoric ester amides of the formula I are obtained when (a) a phosphoramidothioate salt of the general formula

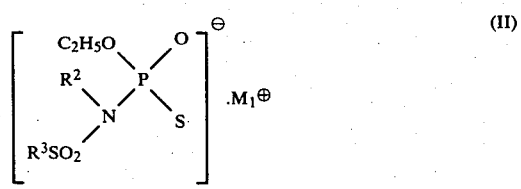

where $R^2$ and $R^3$ have the above meanings and $M_1$ is an alkali metal ion or an ammonium ion, is reacted with an alkylating agent of the formula $$R^1\text{-X-}(CH_2)_n\text{-Y} \qquad (III)$$

where $R^1$, X and n have the above meanings and Y is halogen or a sulfonic acid group, or (b) a thiophosphoryl halide of the formula

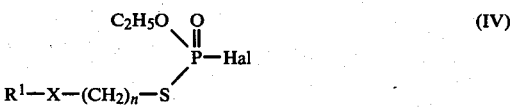

where $R^1$, X and n have the above meanings and Hal is halogen, preferably chlorine, is reacted with a sulfonylamide salt of the formula

where $R^2$ and $R^3$ have the above meanings and $M_2$ is an alkali metal, preferably sodium or potassium.

Examples of suitable alkali metals $M_1$ in formula II are sodium and potassium. For the purposes of the invention, the ammonium ion $M_1^\oplus$ is unsubstituted ammonium, dialkylammonium or trialkylammonium, eg. dimethylammonium, trimethylammonium or triethylammonium, or pyridinium.

Examples of suitable sulfonic acid groups Y in formula III are benzenesulfonate, p-toluenesulfonate, monoethylsulfonate, monobromosulfonate and mono-sec-butylsulfonate.

The phosphoramidothioate salt of the formula II used as a starting material in process (a) can be prepared by reacting a phosphoramidothioate of the formula

where $R^2$ and $R^3$ have the above meanings, with a dealkylating agent of the formula $$R^4SM_1 \qquad (VII)$$

In formula VII, $M_1$ has the above meaning and $R^4$ is hydrogen, alkyl, preferably of 1 to 4 carbon atoms, or alkoxythiocarbonyl, eg. methoxythiocarbonyl or ethoxythiocarbonyl.

Examples of the phosphoramidothioate salts of the formula II are potassium O-ethyl-N-methyl-N-methanesulfonylphosphoramidothioate, potassium O-ethyl-N-methyl-N-ethanesulfonylphosphoramidothioate, potassium O-ethyl-N-methyl-N-(dimethylsulfamyl)-phosphoramidothioate, potassium O-ethyl-N-ethyl-N-methanesulfonylphosphoramidothioate, potassium O-ethyl-N-isopropyl-N-methanesulfonyl-phosphoramidothioate and potassium O-ethyl-N-isopropyl-N-(dimethylsulfamyl)-phosphoramidothioate and the corresponding sodium, triethylammonium, dimethylaniline and pyridinium salts.

Examples of alkylating agents of the formula III are chloromethyl methyl sulfide, chloromethyl ethyl sulfide, 2-chloroethyl methyl sulfide, 2-chloroethyl ethyl sulfide, 2-chloroethyl isopropyl sulfide, 2-chloroethyl methyl ether, 2-chloroethyl ethyl ether and 2-chloroethyl isopropyl ether, and the corresponding bromides, benzenesulfonates and p-toluenesulfonates, as well as ethyl sulfate, diethyl sulfate, butyl sulfate, dibutyl sulfate, sec.-butyl sulfate and di-sec.-butyl sulfate.

Examples of phosphoramidothioates of the formula VI are O,O-diethyl N-methyl N-methanesulfonyl phosporamidothioate, O,O-diethyl N-methyl N-ethanesulfonyl phosphoramidothioate, O,O-diethyl N-methyl N-(dimethylsulfamyl)phosphoramidothioate, O,O-diethyl N-isopropyl N-methanesulfonyl phosphoramidothioate and O,O-diethyl N-isopropyl N-(dimethylsulfamyl)-phosphoramidothioate.

Examples of the dealkylating agents of the formula VII are sodium hydrogen sulfide, potassium hydrogen sulfide, sodium methanethiolate, potassium methanethiolate, potassium methylxanthogenate, potassium ethylxanthogenate and ammonium sulfide.

Process (a) can be represented by the following equation:

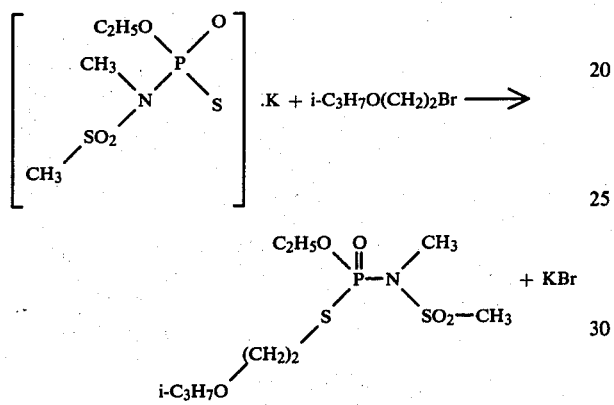

Reaction (a) for the preparation of the compounds of the formula I is preferably carried out in the presence of a solvent or diluent. Examples of such solvents and diluents are water and inert organic solvents, such as aliphatic, alicyclic and aromatic hydrocarbons which may be chlorine-substituted, eg. hexane, cyclohexane, petroleum ether, naphtha, benzene, toluene, xylene, methylene chloride, chloroform, carbon tetrachloride, ethylene chloride, trichloroethylene and chlorobenzene, acyclic and cyclic ethers, eg. diethyl ether, methyl ethyl ether, diisopropyl ether, dibutyl ether, propylene oxide, dioxane and tetrahydrofuran, ketones, eg. acetone, methyl ethyl ketone, methyl isopropyl ketone and methyl isobutyl ketone, nitriles, eg. acetonitrile, propionitrile and acrylonitrile, alcohols, eg. methanol, ethanol, isopropanol, tert.-butanol and ethylene glycol, esters, eg. ethyl acetate and amyl acetate, acid amides, sulfoxides, eg. dimethylsulfoxide, dimethylsulfone, and bases, eg. pyridine.

In the reaction according to (a) the temperature can be varied within a wide range, in general from $-20°$ C. to the boiling point of the mixture, preferably from 0° to 100° C. The reaction is preferably carried out under atmospheric pressure but reduced or superatmospheric pressure can also be employed.

Examples of suitable thiophosphoryl halides of the formula IV are O-ethyl-S-2-methoxyethylthiophosphoryl chloride, O-ethyl-S-2-ethoxyethylthiophosphoryl chloride and O-ethyl-S-2-isopropoxythiophosphoryl chloride.

Examples of salts of the formula V are sodium N-methylmethanesulfonamide, sodium N-methylethanesulfonamide, sodium N-methylisopropanesulfonamide, sodium N-methyldimethylsulfamylamide, sodium N-isopropyldimethylsulfamylamide, and the corresponding potassium salts.

Process (b) can be represented by the following equation:

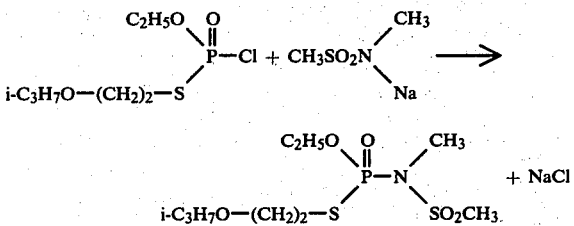

Process (b) is preferably carried out in the presence of an inert solvent or diluent, and the solvents suitable for process (a) can also be used in this case to obtain the desired product in high purity and in good yield.

In the reaction according to (b) the temperature can be varied within a wide range, in general from $-20°$ C. to the boiling point of the mixture, preferably from 0° to 100° C. Although the reaction is advantageously carried out under atmospheric pressure, reduced or superatmospheric pressure can also be employed.

The Examples which follow illustrate the preparation of the compounds of the formula I by processes (a) and (b).

PREPARATION EXAMPLES

Process (a)

10.5 g of sodium N-methylmethanesulfonylamide were suspended in 70 ml of acetonitrile, and 17.3 g of O-ethyl-S-2-isopropoxyethylthiophosphoryl chloride were added dropwise at room temperature. When all had been added, the mixture was heated at 82° C. for 6 hours. The acetonitrile was evaporated off in a rotary evaporator, the residue was mixed with toluene, the mixture was washed with water and 2 N sodium hydroxide solution, and the organic phase was dried over anhydrous sodium sulfate. The solvent and volatile impurities were then removed under reduced pressure (1 mbar) at 40° C. 14.3 g of O-ethyl S-2-isopropoxyethyl N-methyl N-methanesulfonyl phosphoramidothiolate ($n_D^{23} = 1.4859$) in the form of a pale yellow oil were obtained as the residue.

Process (b)

4.48 g of potassium hydroxide were dissolved in 100 ml of ethanol, and gaseous hydrogen sulfide was passed through the solution at room temperature. 20.88 g of O,O-diethyl N-methyl N-methanesulfonyl phosphoramidothioate were added dropwise to the resulting potassium hydrogen sulfide solution, and the mixture was heated at 70° C. for 4 hours. 15.03 g of 2-isopropoxyethyl bromide were added dropwise at 50° C., and the mixture was then heated at 70° C. for 6 hours, with stirring. The solvent and the low-boiling substances were evaporated off in a rotary evaporator, and the residue was worked up as described under (a). 13.7 g of O-ethyl S-2-isopropoxyethyl N-methyl N-methanesulfonyl phosphoramidothiolate ($n_D^{23} = 1.4860$) were obtained in the form of a pale yellow oil.

The following compounds, for example, were prepared by one of the above processes:

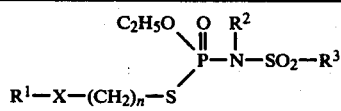

$$R^1-X-(CH_2)_n-S \underset{}{\overset{C_2H_5O}{\diagup}} \overset{O}{\underset{\|}{P}}-\overset{R^2}{\underset{|}{N}}-SO_2-R^3$$

| No. | $R^1$ | $R^2$ | $R^3$ | X | n | $n_D$ |
|---|---|---|---|---|---|---|
| 1 | CH₃ | CH₃ | CH₃ | O | 2 | $n_D^{28}=1.4940$ |
| 2 | C₂H₅ | " | " | O | 2 | $n_D^{22}=1.4902$ |
| 3 | i-C₃H₇ | " | " | O | 2 | $n_D^{23}=1.4860$ |
| 4 | CH₃ | " | N(CH₃)₂ | O | 2 | $n_D^{22}=1.4910$ |
| 5 | C₂H₅ | " | " | O | 2 | $n_D^{25}=1.4841$ |
| 6 | i-C₃H₇ | " | " | O | 2 | $n_D^{25}=1.4805$ |
| 7 | CH₃ | " | C₂H₅ | O | 2 | $n_D^{21}=1.4871$ |
| 8 | C₂H₅ | " | " | O | 2 | $n_D^{21}=1.4861$ |
| 9 | i-C₃H₇ | " | " | O | 2 | $n_D^{21}=1.4850$ |
| 10 | CH₃ | i-C₃H₇ | N(CH₃)₂ | O | 2 | $n_D^{21}=1.4867$ |
| 11 | C₂H₅ | " | " | O | 2 | $n_D^{23}=1.4817$ |
| 12 | i-C₃H₇ | " | " | O | 2 | $n_D^{21}=1.4822$ |

The following compounds, for example, may be prepared by one of the above processes:

| No. | $R^1$ | $R^2$ | $R^3$ | X | n |
|---|---|---|---|---|---|
| 13 | CH₃ | CH₃ | CH₃ | S | 1 |
| 14 | " | C₂H₅ | " | S | 1 |
| 15 | " | i-C₃H₇ | " | S | 1 |
| 16 | " | CH₃ | C₂H₅ | S | 1 |
| 17 | " | CH₃ | N(CH₃)₂ | S | 1 |
| 18 | C₂H₅ | CH₃ | CH₃ | S | 1 |
| 19 | " | C₂H₅ | " | S | 1 |
| 20 | " | i-C₃H₇ | " | S | 1 |
| 21 | " | CH₃ | C₂H₅ | S | 1 |
| 22 | " | CH₃ | N(CH₃)₂ | S | 1 |
| 23 | CH₃ | CH₃ | CH₃ | S | 2 |
| 24 | " | C₂H₅ | " | S | 2 |
| 25 | " | i-C₃H₇ | " | S | 2 |
| 26 | " | CH₃ | C₂H₅ | S | 2 |
| 27 | " | CH₃ | N(CH₃)₂ | S | 2 |
| 28 | " | i-C₃H₇ | " | S | 2 |
| 29 | C₂H₅ | CH₃ | CH₃ | S | 2 |
| 30 | " | C₂H₅ | " | S | 2 |
| 31 | " | i-C₃H₇ | " | S | 2 |
| 32 | " | CH₃ | C₂H₅ | S | 2 |
| 33 | " | CH₃ | N(CH₃)₂ | S | 2 |
| 34 | " | C₂H₅ | " | S | 2 |
| 35 | " | i-C₃H₇ | " | S | 2 |
| 36 | i-C₃H₇ | CH₃ | CH₃ | S | 2 |
| 37 | " | CH₃ | C₂H₅ | S | 2 |
| 38 | i-C₃H₇ | CH₃ | N(CH₃)₂ | S | 2 |
| 39 | CH₃ | C₂H₅ | CH₃ | O | 2 |
| 40 | " | i-C₃H₇ | CH₃ | O | 2 |
| 41 | " | C₂H₅ | C₂H₅ | O | 2 |
| 42 | " | i-C₃H₇ | C₂H₅ | O | 2 |
| 43 | " | CH₃ | i-C₃H₇ | O | 2 |
| 44 | " | C₂H₅ | N(CH₃)₂ | O | 2 |
| 45 | " | CH₃ | N(C₂H₅)₂ | O | 2 |
| 46 | " | CH₃ | N(i-C₃H₇)₂ | O | 2 |
| 47 | C₂H₅ | C₂H₅ | CH₃ | O | 2 |
| 48 | " | i-C₃H₇ | CH₃ | O | 2 |
| 49 | " | C₂H₅ | C₂H₅ | O | 2 |
| 50 | " | i-C₃H₇ | C₂H₅ | O | 2 |
| 51 | " | CH₃ | n-C₃H₇ | O | 2 |
| 52 | " | CH₃ | i-C₃H₇ | O | 2 |
| 53 | " | C₂H₅ | i-C₃H₇ | O | 2 |
| 54 | " | i-C₃H₇ | i-C₃H₇ | O | 2 |
| 55 | " | C₂H₅ | N(CH₃)₂ | O | 2 |
| 56 | " | CH₃ | N(CH₃)₂ | O | 2 |
| 57 | " | CH₃ | N(i-C₃H₇)₂ | O | 2 |
| 58 | i-C₃H₇ | C₂H₅ | CH₃ | O | 2 |
| 59 | i-C₃H₇ | i-C₃H₇ | CH₃ | O | 2 |
| 60 | " | n-C₃H₇ | CH₃ | O | 2 |
| 61 | " | C₂H₅ | C₂H₅ | O | 2 |
| 62 | " | i-C₃H₇ | C₂H₅ | O | 2 |
| 63 | " | CH₃ | n-C₃H₇ | O | 2 |
| 64 | " | " | i-C₃H₇ | O | 2 |
| 65 | " | " | N(CH₃)₂ | O | 2 |
| 66 | " | " | N(i-C₃H₇)₂ | O | 2 |

The N-sulfonylated thiolphosphoric ester amides of the formula I according to the invention are suitable for effectively combating pests from the classes of insects, arachnida and nematodes. They may be used as pesticides for crop protection, and in the hygiene, stores protection and veterinary sector.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae,* and *Aporia crataegi.*

Examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda.*

Examples from the Diptera order are *Lycoria pectoralis, Mayetiola; destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sericata,* and *Hypoderma lineata.*

Examples from the Hymenoptera order are *Athalia rosae, Haplocampa minuta, Monomorium pharaonis, Solenopsis geminata,* and *Atta sexdens.*

Examples from the Heteroptera order are *Nezara viridula, Eurygaster integriceps, Blissus leucopterus, Dysdercus cingulatus, Dysdercus intermedius, Piesma quadrata,* and *Lygus pratensis.*

Examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha* gossypii, Sappaphis mali, Sappaphis mala, Dysaphis radicola, Brachycaudus cardui, Brevicornye brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis, and Viteus vitifolii.

Examples from the Isoptera order are Reticulitermes lucifugus, Calotermes flavicollis, Leucotermes flavipes, and Termes natalensis.

Examples from the Orthoptera order are Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana, and Blabera gigantea.

Examples of mites and ticks (Acarina) belonging to the Arachnida class are Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum, and Boophilus microplus.

Examples from the Nemathelminthes class are root-knot nematodes, e.g., Meloidogyne incognita, Meloidogyne hapla, and Meloidogyne javanica, cyst-forming nematodes, e.g., Heterodera rostochiensis, Heterodera schachtii, Heterodera avenae, Heterodera glycines, and Heterodera trifolii, and stem and leaf eelworms, e.g., Ditylenchus dipsaci, Ditylenchus destructor, Pratylenchus neglectus, Pratylenchus penetrans, Pratylenchus goodeyi, Pratylenchus curvitatus and Tylenchorhynchus dubius, Tylenchorhynchus claytoni, Rotylenchus robustus, Heliocotylenchus multicinctus, Radopholus similis, Belonolaimus longicaudatus, Longidorus elongatus, and Trichodorus primitivus.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, alphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalensulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products or sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 3 parts by weight of compound no. 1 is intimately mixed with 97 parts by weight of particulate kaolin. A dust is obtained containing 3% by weight of the active ingredient.

II. 30 parts by weight of compound no. 10 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 12 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 8 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 3 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

The amount of active ingredient applied in the open may vary from 0.2 to 10 kg/ha, and is preferably from 0.5 to 2.0 kg/ha.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropane+1,2-dichloropropane, 1,2-dibromoethane, 2-sec-butylphenyl-N-methylcarbamate, o-chlorophenyl-N-methylcarbamate, 3-isopropyl-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N',N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimthyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphoshporoamidothioate, O,S-dimethyl-N-acetylphosphoramidothioate, alpha-hexachlorocyclohexane, 1,2-di-(p-methoxyphenyl)2,2,2-trichloroethane, 6,7,8,9,10,10-hexachloro- 1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropancarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

The following examples demonstrate the biological action of the new compounds. The active ingredients used for comparison purposes was O-ethyl-S-n-propyl-N-methyl-N-methanesulfonyl phosphoramidothiolate (German Laid-Open Application DOS No. 2,642,054).

The active ingredients are numbered as in the table above.

EXAMPLE 1

Breeding experiment with Mediterranean fruit flies
(*Ceratitis capitata*)

The experiment was carried out in 100 ml plastic beakers filled with 40 g of a nutrient medium of carrot powder and water (1:3), with yeast added. The active ingredient was stirred into the medium as an aqueous formulation, and the medium was then inoculated with from 100 to 200 fresh eggs. The beakers were kept closed at 24° to 26° C.; after about a week, the development was able to be assessed.

In this test, active ingredients nos. 1, 2, 3, 5 and 6 had a good action.

EXAMPLE 2

Contact action and effect of ingested food on caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

In this test, for example active ingredients nos. 1, 2 and 3 had a better action than the comparative agent.

EXAMPLE 3

Contact action on oriental cockroaches (*Blatta orientalis*)

The bottoms of 1 liter preserving jars was lined with acetonic solutions of the active ingredients. After the solvent had evaporated, 5 adult cockroaches were introduced into each jar. The kill rate was determined after 48 hours.

In this test, active ingredients nos. 1, 2, 3, 4, 5 and 6 had an excellent action.

EXAMPLE 4

Contact action on ticks (*Ornithodorus moubata*)

Ticks in the 3rd larval stage were placed in paper bags and dipped for 3 seconds in the emulsion under investigation. The bags were then suspended. The action on the ticks was assessed after 48 hours.

In this test, active ingredients nos. 1, 2, 3 and 6 had a better action than the comparative agent.

EXAMPLE 5

Contact action on bean aphids (*Aphis fabae*), spray experiment

Potton bean plants (*Vicia faba*) with extensive bean aphid colonies were sprayed to runoff in a spray booth with aqueous formulations of the active ingredients. Assessment took place after 48 hours.

In this test, active ingredients nos. 1, 2, 3, 5 and 6 had a good action.

EXAMPLE 6

Contact action on cotton stainers (*Dysdercus intermedius*)

Petri dishes 10 cm in diameter were lined with 1 ml of acetonic solutions of the active ingredients. After the solvent had evaporated, 20 larvae of the penultimate stage were placed in the dishes, and the effect was registered after 24 hours.

In this test, active ingredients nos. 1, 2, 3, 4, 5 and 6 had a good action.

EXAMPLE 7

Action on eggs of the diamondback moth (*Plutella maculipennis*)

Young cabbage plants having 2 to 3 pairs of leaves on which large number of eggs of the diamondback moth had been laid were sprayed to runoff with aqueous emulsions of the active ingredients.

The plants were then kept under greenhouse conditions, and the leaf area eaten by the caterpillars which hatched out was noted.

In this test, active ingredients nos. 1, 2, 3, 4 and 5 had a good action.

EXAMPLE 8

Contact action on Rhodnius bugs (*Rhodnius prolixus*)

Petri dishes 10 cm in diameter were lined with 1 ml of acetonic solutions of the active ingredients. After the solvent had evaporated, 10 adult bugs were placed in the dishes.

The action was assessed after 24 hours.

In this test, active ingredients nos. 2 and 3 had a better action than the comparative agent.

EXAMPLE 9

Action on spider mites (*Tetranychus telarius*)

Potted bush beans which had developed the first pair of true leaves and were under heavy attack from spider mites (Tetranychus telarius) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

In this test, active ingredients nos. 1, 2, 3, 5 and 6 had a better action than the comparative agent.

EXAMPLE 10

Action on root-knot nematodes (*Meloidogyne incognita*) in tomatoes 30 ml of aqueous formulations of the active ingredients was intimately mixed with 300 g of mold heavily infested with Meloidogyne incognita. The mold was then filled into plastic pots and a tomato seedling planted therein.

The roots were checked for root-knots after 8 weeks.

In this test, active ingredients nos. 1, 2, 3, 4 and 6 had a very good action.

We claim:

1. An N-sulfonylated thiolphosphoric ester amide of the formula $$\begin{array}{c} C_2H_5O \\ \diagdown \\ R^1-X-(CH_2)_{\overline{n}}-S \end{array} \!\!\!\! \begin{array}{c} O \\ \| \\ P-N-SO_2-R^3 \\ \diagup \end{array} \!\!\!\! \begin{array}{c} R^2 \\ | \\ \end{array} \quad (I)$$

where $R^1$ is alkyl of 1 to 3 carbon atoms, $R^2$ is alkyl of up to 6 carbon atoms, $R^3$ is alkyl of 1 to 6 carbon atoms or dialkylamino where alkyl is of 1 to 6 carbon atoms, X is oxygen or sulfur, and n is 1 or 2.

2. O-Ethyl-S-(2-methoxy-ethyl)-N-methyl-N-methane-sulfonyl phosphoramidothiolate.

3. O-Ethyl-S-(2-ethoxy-ethyl)-N-methyl-N-methane-sulfonyl phosphoramidothiolate.

4. O-Ethyl-S-(2-isopropoxy-ethyl)-N-methyl-N-methane-sulfonyl phosphoramidothiolate.

5. An insecticidal, acaricidal and nematicidal agent containing inert additives and an N-sulfonylated thiolphosphoric ester amide of the formula I as defined in claim 1.

6. An insecticidal, acaricidal and nematicidal agent containing inert additives and, as active ingredient, O-ethyl-S-(2-methoxy-ethyl)-N-methyl-N-methane-sulfonyl phosphoramidothiolate.

7. An insecticidal, acaricidal and nematicidal agent containing inert additives and, as active ingredient, O-ethyl-S-(2-ethoxy-ethyl)-N-methyl-N-methane-sulfonyl phosphoramidothiolate.

8. An insecticidal, acaricidal and nematicidal agent containing inert additives and, as active ingredient, O-ethyl-S-(2-isopropoxy-ethyl)-N-methyl-N-methane-sulfonyl phosphoramidothiolate.

9. A process for combating insects, arachnida and/or nematodes, wherein an effective amount of an N-sulfonylated thiolphosphoric ester amide of the formula I as defined in claim 1 is allowed to act on them and/or their habitat.

* * * * *